US012779182B2

(12) United States Patent
Liu et al.

(10) Patent No.: US 12,779,182 B2
(45) Date of Patent: Nov. 3, 2026

(54) BALLOON STENT

(71) Applicant: Lepu Medical Technology (Beijing) Co., Ltd., Beijing (CN)

(72) Inventors: Pengfei Liu, Beijing (CN); Zhongjie Pu, Beijing (CN); Yuxin Zhang, Beijing (CN); Chuan Wang, Beijing (CN)

(73) Assignee: Lepu Medical Technology (Beijing) Co., Ltd., Beijing (CN)

( * ) Notice: Subject to any disclaimer, the term of this patent is extended or adjusted under 35 U.S.C. 154(b) by 487 days.

(21) Appl. No.: 16/627,382

(22) PCT Filed: Aug. 30, 2019

(86) PCT No.: PCT/CN2019/103690

§ 371 (c)(1),
(2) Date: Dec. 30, 2019

(87) PCT Pub. No.: WO2021/031244

PCT Pub. Date: Feb. 25, 2021

(65) Prior Publication Data

US 2022/0118233 A1 Apr. 21, 2022

(51) Int. Cl.
*A61F 2/958* (2013.01)
*A61F 2/82* (2013.01)
(Continued)

(52) U.S. Cl.
CPC ............. *A61M 25/10* (2013.01); *A61F 2/958* (2013.01); *A61F 2002/826* (2013.01);
(Continued)

(58) Field of Classification Search
CPC ................ A61F 2/958; A61F 2002/826; A61F 2002/91558; A61F 2002/91566;
(Continued)

(56) References Cited

U.S. PATENT DOCUMENTS 5,122,154 A * 6/1992 Rhodes ..................... A61F 2/86
606/198
5,593,417 A * 1/1997 Rhodes ..................... A61F 2/86
606/198
(Continued)

FOREIGN PATENT DOCUMENTS

CN 201350139 Y 11/2009
CN 106466205 A 3/2017
(Continued)

OTHER PUBLICATIONS

Office Action dated Mar. 3, 2021 for corresponding CN App No. 201910821808.9 and English Translation.
(Continued)

*Primary Examiner* — Jing Rui Ou
(74) *Attorney, Agent, or Firm* — Elmore Patent Law Group, P.C.; Joseph C. Zucchero; Carolyn S. Elmore

(57) ABSTRACT

The present application discloses a balloon stent, comprising a drug balloon and a stent assembly, each having a contracted state and an expanded state, wherein the stent assembly includes at least two stents sleeved around a periphery of the drug balloon and disposed at an interval along its axial direction. The stent assembly adopts a design of at least two stents disposed at an interval, which can effectively reduce coverage of the stents and volume of implant, and reduce the probability of restenosis. When restenosis occurs, the stent can be re-implanted for treatment in the interval between two adjacent stents. The newly implanted stent will not overlap with the original stent, so as to effectively suppress the occurrence of in-stent restenosis and ensure long-term treatment effect.

8 Claims, 2 Drawing Sheets

(51) Int. Cl.
*A61F 2/915* (2013.01)
*A61M 25/10* (2013.01)

(52) U.S. Cl.
CPC ............... *A61F 2002/91558* (2013.01); *A61F 2002/91566* (2013.01); *A61F 2210/0076* (2013.01); *A61F 2250/0067* (2013.01); *A61M 2025/105* (2013.01)

(58) Field of Classification Search
CPC .... A61F 2210/0076; A61F 2250/0067; A61M 25/10; A61M 2025/105
See application file for complete search history.

(56) References Cited

U.S. PATENT DOCUMENTS

| | | | | |
|---|---|---|---|---|
| 5,893,840 | A * | 4/1999 | Hull | A61F 2/958 606/192 |
| 6,022,359 | A * | 2/2000 | Frantzen | A61F 2/958 606/108 |
| 6,187,034 | B1 | 2/2001 | Frantzen | |
| 10,993,824 | B2 * | 5/2021 | Longo | A61F 2/966 |
| 2003/0181973 | A1 * | 9/2003 | Sahota | A61L 31/16 623/1.42 |
| 2004/0215312 | A1 * | 10/2004 | Andreas | A61F 2/958 623/1.11 |
| 2005/0085888 | A1 | 4/2005 | Andreas et al. | |
| 2009/0105686 | A1 * | 4/2009 | Snow | A61F 2/958 604/509 |
| 2013/0268045 | A1 | 10/2013 | Papp et al. | |
| 2018/0042740 | A1 | 2/2018 | Schwartz et al. | |
| 2018/0207008 | A1 | 7/2018 | Giasolli et al. | |
| 2020/0038206 | A1 | 2/2020 | Santos et al. | |
| 2020/0352753 | A1 | 11/2020 | Giasolli et al. | |

FOREIGN PATENT DOCUMENTS

| | | | |
|---|---|---|---|
| CN | 107847330 | A | 3/2018 |
| CN | 108295360 | A | 7/2018 |
| CN | 110087587 | A | 8/2019 |
| WO | 2019165311 | A1 | 8/2019 |

OTHER PUBLICATIONS

English Translation of Office Action dated Aug. 18, 2021 for corresponding CN App No. 201910821808.9.
Office Action dated Aug. 18, 2021 for corresponding CN App No. 201910821808.9.
International Search Report of PCT/CN2019/103690 dated Jun. 4, 2020.
Written Opinion of PCT/CN2019/10369 dated Jun. 4, 2020.
English Translation of a Decision of Rejection dated Mar. 25, 2022 for corresponding CN App No. 201910821808.9.
Extended European Search Report of EP19823758.8, dated Feb. 8, 2024.

* cited by examiner

BALLOON STENT

RELATED APPLICATIONS

This application U.S. National stage entry of International Application No. PCT/CN2019/103690, which designated the United States and was filed on Aug. 30, 2019. The entire teachings of the above application are incorporated herein by reference.

TECHNICAL FIELD

The present application relates to the technical field of medical instruments, and in particular to a balloon stent.

BACKGROUND

A stent is the most important means for clinical treatment of diseases caused by stenosis or blockage of blood vessels. It can achieve a purpose of expanding the blood vessels in the lesion area to restore normal blood flow, and further prevent restenosis caused by vasoconstriction. The current coronary stent implantation pathway applies a minimally invasive method to send a coronary stent to the vascular stenosis area mainly through a radial artery and a femoral artery.

However, after the current stent is implanted into human body, it may stimulate the intimal hyperplasia as a foreign body, thus easily incurring in-stent restenosis after a long period of time. The in-stent restenosis is a pathophysiological evolution process, which is different from restenosis in histology and characterized by neointimal formation. Even if a resistant drug for inhibiting the intimal hyperplasia is coated on the surface of the stent, the phenomenon of in-stent restenosis will still occur. Moreover, there is no effective treatment method once the in-stent restenosis occurs. If another drug stent is internally installed in the restenotic drug stent, the probability of in-stent restenosis is as high as 43%. At present, there is no effective way to solve this problem.

Therefore, the current treatment methods of stent implantation are prone to restenosis, poor long-term treatment effects, and difficult to perform secondary stent implantation.

Drug-eluting balloon (DEB) is a kind of interventional therapy that has developed rapidly and is widely used recently. After being implanted into the human body, the drug balloon expands the blood vessels in the lesion and targets the drug to concentrate there, thereby inhibiting production of the neointimal in the blood vessels and reducing the probability of restenosis.

However, the drug-eluting balloon has the problems of requiring multiple treatments and only having short-term effect, and cannot prevent the occurrence of acute elastic shrinkage of the blood vessel wall due to lack of support of the metal skeleton, thereby causing pain and life-threatening to patients.

Therefore, there is a need to provide an implantable drug-loaded therapeutic device with good long-term treatment effect and less prone to restenosis.

SUMMARY

Therefore, the technical problem to be solved by the present application is to overcome the technical problems that the implantable stent in the prior art is prone to restenosis, poor long-term treatment effect, and difficult to perform secondary treatment, thereby providing a balloon stent.

To solve the above technical problems, the present application provides the following technical solution.

A balloon stent comprises a drug balloon and a stent assembly, each having a contracted state and an expanded state, wherein the stent assembly includes at least two stents sleeved around a periphery of the drug balloon and disposed at an interval along its axial direction.

Preferably, the interval between two adjacent stents is larger than a length of the stent.

Preferably, the length of the stent is 2-30 mm, and the interval between the two adjacent stents is 3-50 mm.

Preferably, when inflated, the drug balloon is in the expanded state and expands the stent assembly; and in the expanded state, an outer surface of the stent assembly is adapted to contact surrounding tissues.

Preferably, the stent is a tubular structure, and has a hollow-out structure of an outer wall.

Preferably, the hollow-out structure comprises a plurality of through holes.

Preferably, the stent is provided with a first drug coating on an outer surface thereof.

Preferably, the first drug coating comprises an active drug selected from one or more of an anti-intimal hyperplasia drug, an anticoagulant drug, and an anti-platelet adhesion drug, an anti-infective drug, an antibacterial drug, an anti-inflammatory response drug and an anti-allergic drug.

Preferably, the active drug is selected from one or more of paclitaxel, docetaxel, rapamycin and derivatives thereof, statins, aspirin, warfarin, heparin, low molecular-weight heparin and cilostazol.

Preferably, the drug balloon is provided with a second drug coating on a surface thereof.

Preferably, the stent is made of one of stainless steel, cobalt-chromium alloy, nickel-titanium alloy, fully degradable poly-L-lactic acid, magnesium alloy, and zinc alloy.

The technical solution of the present application has the following advantages.

1. The present application provides a balloon stent comprising a drug balloon and a stent assembly. When the balloon stent is not in use, the drug balloon is sleeved on the outer periphery of the stent assembly; when the balloon stent is in use, the drug balloon is deflated and then will be separated from the stent assembly. The stent assembly adopts a design of at least two stents disposed at an interval, which can effectively reduce coverage of the stents and volume of implant, and reduce the probability of restenosis; even if restenosis occurs, a stent can be re-implanted in the interval between two adjacent stents for treatment. The newly implanted stent will not overlap with the original stent, so as to effectively suppress the occurrence of in-stent restenosis and ensure long-term treatment effect.

2. In the balloon stent provided by the present application, the drug balloon can expand the blood vessels in the lesion at the initial stage of implantation and target the drug, thereby achieving the purpose of expanding the blood vessel and restoring blood flow, reducing intimal hyperplasia and treating stenosis of blood vessels.

3. In the balloon stent provided by the present application, the stent assembly has multiple stents disposed at an interval. Compared with an integrated stent, the stent assembly of this application has better compliance, and can produce large deformation under the action of a small external force, thereby making the balloon stent have unique advantages to treat bifurcation disease, small vessel disease and complex physiological environment disease.

4. The balloon stent provided by the present application can effectively solve the problems of short duration of drug balloon treatment and easy recurrence of the disease, so as to play a role of supporting stenotic blood vessels for a long time to ensure long-term treatment effect.

DESCRIPTION OF THE DRAWING

In order to more clearly illustrate the technical solutions of the embodiments of the present application or the prior art, the drawings involving in the embodiments of the present application or the prior art will be briefly described below. Obviously, the drawings in the following description are only some embodiments of the present application, and those skilled in the art can obtain other drawings based on these drawings without any creative efforts.

In the figures, the reference numerals are.

1. drug balloon; 2. stent.

DETAILED DESCRIPTION OF THE EMBODIMENTS

The technical solutions of the present application will be described clearly and completely with reference to the accompanying drawings. It is obvious that the described embodiments are only a part of the embodiments of the present application, but not all of the embodiments. All other embodiments obtained by those skilled in the art based on the embodiments of the present application without any creative efforts are within the scope of the present application.

Figure 1:
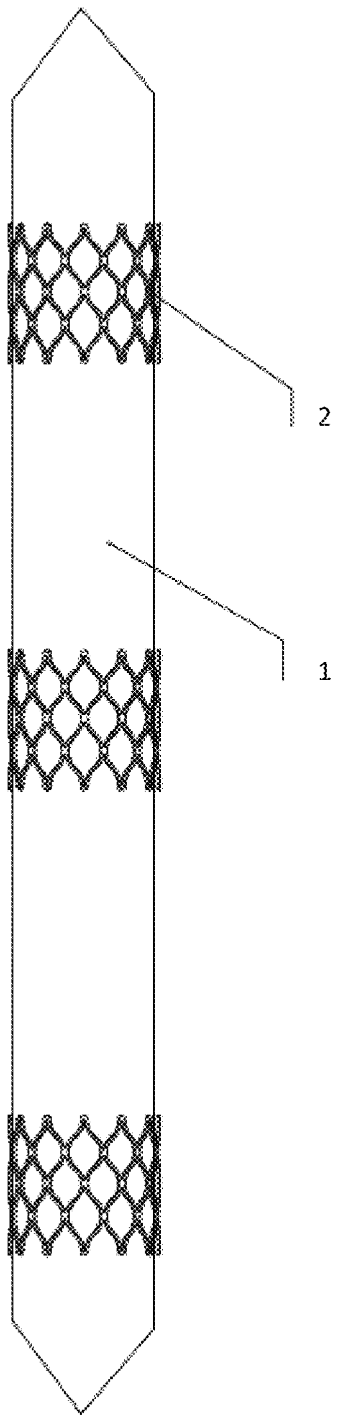
FIG. 1 is a schematic structural diagram of a balloon stent according to an embodiment of the present application.

As shown in FIG. 1, a balloon stent comprises a drug balloon 1 and a stent assembly, each having a contracted state and an expanded state. The stent assembly includes at least two stents 2 sleeved around a periphery of the drug balloon 1 in an unused state, and the at least two stents 2 are disposed at an interval along the axial direction of the stents 2.

In the embodiment, there are three stents 2 arranged at even intervals. After the stent assembly is implanted into the human blood vessel, the three stents 2 are supported at two ends and middle positions of the diseased blood vessel segment, respectively. The structure of the stent assembly can provide stable support throughout the diseased blood vessel segment, so as to ensure good support effect. In other embodiment, the number and length of the stent 2 and the interval between adjacent stents 2 can be adaptively adjusted according to the diameter of the blood vessel segment and the length of the diseased blood vessel segment.

In the balloon stent 2, the stent assembly adopts a design of multiple stents 2 disposed at an interval, which can effectively reduce coverage of the stents 2 and volume of implant, and reduce the probability of restenosis; even if restenosis occurs, the stent 2 can be re-implanted in the interval between two adjacent stents 2 for treatment. The newly implanted stent 2 will not overlap with the original stent 2, so as to effectively suppress the occurrence of in-stent restenosis and ensure long-term treatment effect. Moreover, the stent assembly has multiple stents 2 disposed at an interval. Compared with an integrated stent, the stent assembly has better compliance, and can produce a large deformation under the action of a small external force, thereby reducing the problem of vascular injury or rupture due to the excessive force exerted by the stent 2 on the blood vessel wall during the expansion process in the treatment of some small-diameter diseased blood vessels. Therefore, the balloon stent 2 has unique advantages to treat bifurcation disease, small vessel disease and complex physiological environment disease. In a preferred implementation of the embodiment, the interval between two adjacent stents 2 is larger than a length of the stent 2 in the axial direction. Specifically, when the stent assembly is implanted into a human coronary artery, the length of the stent 2 is 2-30 mm, the interval between two adjacent stent 2 is 3-50 mm, preferably greater than the length of the stents 2 by 1 mm. For example, the interval between two stents 2 is 3 mm when the length of the stents 2 is 2 mm, and the interval between two stents is 5 mm when the length of the stents 2 is 4 mm, so as to be convenient to leave enough space between the original implants for implantation of the new stent 2, thus avoiding the overlapping of the new implanted stent 2 and the original implanted stent 2, thereby reducing the probability of in-stent restenosis. At the same time, such design avoids the length of the stent 2 to be short, thus reducing the probability of elastic shrinkage of the diseased blood vessel segment due to insufficient support of the stent 2.

In the embodiment, when inflated, the drug balloon 1 is in the expanded state and expands the stent assembly; and in the expanded state, an outer surface of the stent assembly is adapted to contact an inner wall of the diseased blood vessel segment.

The stent assembly contacts the diseased blood vessel segment after being expanded under the force of drug balloon 1, so as to provide good support for the diseased blood vessel segment, thereby avoiding the phenomenon of elastic shrinkage of the diseased blood vessel segment, and ensuring the smooth flow of blood in the blood vessel.

Figure 2:
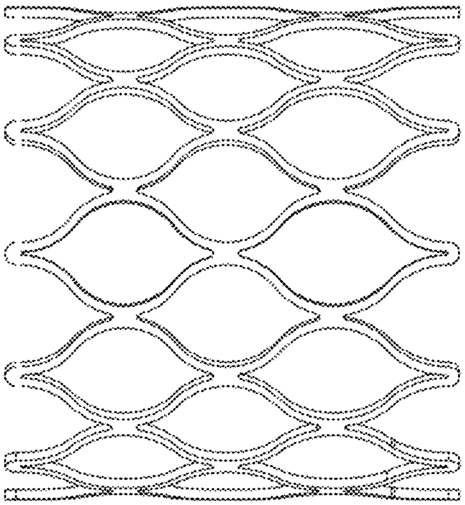
FIG. 2 is a schematic structural diagram of a stent provided by an embodiment of the present application.
Figure 3:
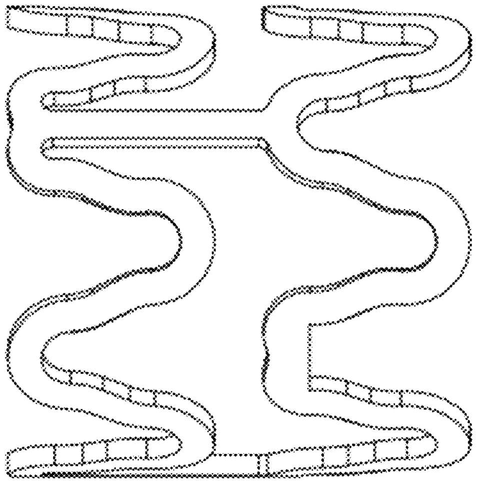
FIG. 3 is a schematic structural diagram of a stent provided by another embodiment of the present application.

In the embodiment, the stent 2 is a tubular structure and has a hollow-out structure of an outer wall. The hollow-out structure comprises through holes. In a specific implementation of the embodiment, as shown in FIG. 2, the stent 2 has a grid-like hollow-out outer wall, and the grid is circular. In another specific implementation of the embodiment, as shown in FIG. 3, the stent 2 has an outer wall including multiple rows of V-shaped corrugated rings and U-shaped corrugated rings arranged alternately in order. Adjacent two rows of corrugated rings are connected through several I-shaped connection keys which are arranged at peak or trough of the V-shaped corrugated rings and the U-shaped corrugated rings. The stent 2 has a more compact structure, and is easier to be expanded in the axial direction. The expanded stent 2 has a higher metal coverage, which can improve a radial support force of the stent 2 within the diseased blood vessel segment. Moreover, after the stent 2 is expanded, the pressure on the blood vessels is more uniform. It should be explained here that the specific geometric structure of the stent can be adaptively selected.

In the embodiment, the stent 2 is provided with a first drug coating on an outer surface thereof. The first drug coating can be applied to the outer surface of the stent 2 or filled in a groove on the outer surface of the stent 2, and comprises an active drug selected from one or more of an anti-intimal hyperplasia drug, an anticoagulant drug, and an anti-platelet adhesion drug, an anti-infective drug, an antibacterial drug, an anti-inflammatory response drug and an anti-allergic drug. Specifically, the active drug is selected from one or more of paclitaxel, docetaxel, rapamycin and derivatives thereof, statins, aspirin, warfarin, heparin, low molecular-weight heparin and cilostazol.

In the embodiment, the stent 2 is made of one of stainless steel, cobalt-chromium alloy, nickel-titanium alloy, fully degradable poly-L-lactic acid, magnesium alloy, and zinc alloy. Compared with ordinary stent made of stainless steel, the stent assembly made of cobalt-chromium alloy or nickel-titanium alloy with the same size has greater radial supporting force, thereby overcoming the problem of insufficient radial support when the multiple stents disposed at an interval support the diseased blood vessel segment. When the stent assembly is made of fully degradable poly-L-lactic acid, the stent 2 can be completely degraded in the blood vessel after a certain period of time, thereby reducing the problem of in-stent stenosis after the active drug on stent 2 is depleted.

In some implementations of the embodiment, the drug balloon 1 is made of a highly compliant balloon. The drug balloon 1 is provided with a second drug coating comprising active drug with the same type as the first drug coating on a surface thereof. When drug balloon 1 in the inflated state expands the diseased blood vessel segment, the second drug coating of the drug balloon 1 can target the drug to the diseased blood vessel segment, thereby achieving the purpose of expanding the blood vessel and restoring blood flow, reducing intimal hyperplasia and treating stenosis of blood vessels.

In summary, the balloon stent provided by the embodiment of the present application includes drug balloon 1 and stent assembly. Moreover, the stent assembly adopts a design of multiple stents 2 disposed at an interval, which not only reduces the problems of prone to in-stent restenosis, poor long-term treatment effect, and difficult to perform secondary treatment in the manner of implanting stent 2 alone, but also solves the problem of short duration of treatment and easy to relapse in the prior method of implanting drug balloon, thereby having advantages of low probability of in-stent restenosis and good long-term treatment effect.

It is apparent that the above embodiments are merely examples for clarity of illustration, and are not intended to limit the embodiments. Other variations or modifications in various forms may be made by those skilled in the art in view of the above description. There is no need and no way to present all of the embodiments therein. The obvious variations or modifications derived therefrom are still within the scope of protection of the present application.

The invention claimed is:

1. A balloon stent assembly, comprising a drug balloon (1) and a stent assembly, each having a contracted state and an expanded state, wherein the stent assembly includes at least two adjacent stents (2) sleeved around a periphery of the drug balloon (1) and disposed at an interval along its axial direction;

wherein a length of each stent of the at least two adjacent stents is 2-30 mm;

wherein the interval between the at least two adjacent stents (2) is greater than the length of each stent of the at least two adjacent stents (2) by 1 mm;

wherein the at least two adjacent stents (2) have an outer wall including multiple rows of V-shaped corrugated rings and U-shaped corrugated rings arranged alternately in order; and adjacent two rows of corrugated rings are connected through I-shaped connection key which is arranged at peak or trough of the V-shaped corrugated rings and the U-shaped corrugated rings; and wherein the at least two adjacent stents (2) are provided with a first drug coating on an outer surface thereof, the first drug coating is filled in a groove on the outer surface of the at least two adjacent stents (2).

2. The balloon stent assembly according to claim 1, wherein when inflated, the drug balloon is in the expanded state and expands the stent assembly; and in the expanded state, an outer surface of the stent assembly is adapted to contact surrounding tissues.

3. The balloon stent assembly according to claim 1, wherein the at least two adjacent stents (2) are a tubular structure, and have a hollow-out structure of an outer wall.

4. The balloon stent assembly according to claim 3, wherein the hollow-out structure comprises a plurality of through holes.

5. The balloon stent assembly according to claim 1, wherein the first drug coating comprises an active drug selected from one or more of an anti-intimal hyperplasia drug, an anticoagulant drug, and an anti-platelet adhesion drug, an anti-infective drug, an antibacterial drug, an anti-inflammatory response drug and an anti-allergic drug.

6. The balloon stent assembly according to claim 5, wherein the active drug is selected from one or more of paclitaxel, docetaxel, rapamycin and derivatives thereof, statins, aspirin, warfarin, heparin, low molecular-weight heparin and cilostazol.

7. The balloon stent assembly according to claim 1, wherein the drug balloon (1) is provided with a second drug coating on a surface thereof.

8. The balloon stent assembly according to claim 1, wherein the at least two adjacent stents (2) are made of one of stainless steel, cobalt-chromium alloy, nickel-titanium alloy, fully degradable poly-L-lactic acid, magnesium alloy, and zinc alloy.

* * * * *